United States Patent [19]

Ciganek

[11] Patent Number: 5,306,821
[45] Date of Patent: Apr. 26, 1994

[54] PROCESS FOR THE PREPARATION OF TERTIARY CARBINAMINES

[75] Inventor: Engelbert Ciganek, Kennett Square, Pa.

[73] Assignee: The Du Pont Merck Pharmaceutical Company, Wilmington, Del.

[21] Appl. No.: 819,429

[22] Filed: Jan. 10, 1992

[51] Int. Cl.$^5$ ............................................. C07D 409/00
[52] U.S. Cl. .................................... 546/212; 546/213; 546/194; 546/329; 549/29; 549/60; 549/429; 549/472; 564/315; 564/336; 564/384; 564/490; 558/418; 558/422; 560/37; 560/155
[58] Field of Search ............... 564/490, 336, 337, 384; 546/212, 333, 329, 213, 194, 329; 549/429, 472, 60, 29

[56] References Cited

U.S. PATENT DOCUMENTS 5,019,650  5/1991  Ciganek et al. ..................... 540/609

OTHER PUBLICATIONS

Imamoto et. al., J. Am. Chem. Soc., 1989, 111, 4392–4398.
Gauthier et. al, J. of organometallic Chem., 140, 1977, 245–255.
Krimen and Cota, Org. React., 1969, 17:213.
Gautier et al., Bull. Soc. Chim. France., 1968, 2916.
Layer, Chem. Rev., 1963, 63:489.
Alvernhe and Laurent, Tetrahedron Lett., 1973, 1057.
Henze et al., J. Am. Chem. Soc., 1943, 65:87.
Henze et al., J. Am. Chem. Soc., 1943, 65:1422.
Henze et al., J. Am. Chem. Soc., 1951, 73:4915.
Allen and Henze, J. Am. Chem. Soc., 1939, 61:1790.
Henze and Swett, 1951, 73:4918.
Chastrette et al., Tetrahedron Lett., 1977, 1:23.
Chastrette and Axiotis, Synthesis, 1980, 889.
Amouroux and Axiotis, Synthesis, 1981, 270.
Neuvonen and Pihlaja, J. Chem. Soc. Perkin Trnsl. II., 1988, 461.
Woodburn and Lathroum, J. Org. Chem., 1954, 19:285.
Pornet and Miginiac, Bull. Soc. Chim. France, 1975, 841.
Davis and Mancinelli, J. Org. Chem., 1977, 42(2):398.
Lipshutz et al., Tetrahedron Lett., 1986, 27(36):4241.
Gauthier et al., J. Organomet. Chem., 1977, 140:245.
Rehberg and Henze, J. Am. Chem. Soc., 1941, 63:2785.
Imamoto et al., J. Org. Chem., 1984, 49:3904.
Imamoto et al., J. Am. chem. Soc., 1989, 111:4392.
Roetz et al., Agnew. Chem. Int. Ed. Engl. 1991, 30:103.
Denmark et al., J. Am. Chem. Soc., 1987, 109:2224.
Weber et al., Synlett, 1989, p. 20.
Fujioka et al., Chem. Pharm. Bull., 1989, 37:602.
Ukaji et al., Chemistry Lett., 1991, p. 173.
Patai, ed., Chemistry of the Carbon–Nitrogen Double Bond, 1970, ch. 6–8.

*Primary Examiner*—Allen J. Robinson
*Assistant Examiner*—Shailendra Kumar
*Attorney, Agent, or Firm*—Gildo E. Fato

[57] ABSTRACT

This invention relates to a novel process for the preparation of tertiary carbinamines by double addition of organolanthanide reagents, especially organocerium reagents, to nitriles. It further relates to the preparation of such amines by the addition of organolanthanide reagents to imines.

14 Claims, No Drawings

PROCESS FOR THE PREPARATION OF TERTIARY CARBINAMINES

FIELD OF THE INVENTION

This invention relates to a novel process for the preparation of tertiary carbinamines by double addition of organolanthanide reagents, especially organocerium reagents, to nitriles. It further relates to the preparation of such amines by the addition of organolanthanide reagents to imines.

BACKGROUND OF THE INVENTION

Tertiary carbinamines (amines wherein one bond from nitrogen is to a tertiary carbon atom) are usually prepared by the addition of carbocations to nitriles [the Ritter reaction: Krimen and Cota, *Org. React.* 17, 213 (1969)]. This reaction requires strongly acidic conditions. In addition, the resulting acyl derivatives of the tertiary carbinamines are often difficult to hydrolyze, necessitating strongly basic conditions. The Ritter reaction is thus limited to substrates that can tolerate both strongly acidic and strongly basic conditions. Reaction of diarylketoximes with sodium in liquid nitrogen followed by alkylation gives tertiary carbinamines but the reaction is limited in scope [Gautier et al., *Bull. Soc. Chim. France*, 1968, 2916].

Addition of organometallic reagents, such as organolithium compounds or Grignard reagents, to nitriles usually gives imines [Layer, *Chem. Rev.* 63, 489 (1963); "Chemistry of the Carbon-Nitrogen Double Bond," S. Patai, Ed. Interscience, New York, N.Y., 1970, chapters 6–8]. Double addition of these reagents to nitriles to give tertiary carbinamines has been reported in only a few isolated and special cases. Thus some Grignard reagents add twice to nitriles in refluxing toluene, but imines are usually the major products and the reaction fails with benzonitrile and phenylacetonitrile [Alvernhe and Laurent, *Tetrahedron Lett.* 1973, 1037]. Allylmagnesium halides add twice to nitriles [Henze et al., *J. Am. Chem. Soc.*, 65, 87, 1422 (1943); 73, 4915 (1951)], as do Grignard reagents to α-alkoxynitriles [Henze et al *J. Am. Chem. Soc.* 61, 1790 (1939); 73, 4915 (1951); Chastrette et al., *Tetrahedron Lett.* 1977, 23; *Synthesis*, 1980, 889; Amouroux and Axiotis, *Synthesis* 1981, 270], 2-hydroxybenzonitrile [Neuvonen and Pihlaja, *J. Chem. Soc. Perkin* 1 1988, 461] and cyanogen [Woodburn and Lathroum, *J. Org. Chem.* 19, 285 (1954)]. α,α-Dibutylbenzylamine is formed in low yield in the reaction of benzonitrile with n-butyllithium at room temperature [Pornet and Miginiac, *Bull. Soc. Chim. France*, 1975, 841].

Organometallic reagents such as organolithium compounds and Grignard reagents, do not normally add to unsubstituted imines ($R_2C=NH$). Tertiary carbinamines have been prepared by replacing the hydrogen atom in these imines with functionalities such as arylsulfenyl [Davis and Mancinelli, *J. Org. Chem.*, 42, 398 (1977)] or acyl [Lipshutz et al., *Tetrahedron Lett.* 27, 4241 (1986)], but it is often difficult to remove these functionalities. The imine salts obtained on addition of alkyl Grignard reagents to α-alkoxynitriles react with alkyl or aryllithium reagents to give tertiary carbinamines [Gauthier et al. *J. Organomet. Chem.* 140, 245 1977)], but the reaction fails with other nitriles. The products obtained on addition of methyl or ethylmagnesium iodide to benzoylacetonitrile, $C_6H_5COCH_2CMe(Et)=NH$, react with allylmagnesium bromide to give the corresponding tertiary carbinamines [Rehberg and Henze, *J. Am. Chem. Soc.*, 63, 2785 (1941)].

The preparation of tertiary carbinamines by addition of organocerium reagents to nitriles or N-unsubstituted imines is new. The reaction of 4-cyanoacetophenone with the reagent prepared from anhydrous cerium chloride and n-butyllithium is reported to give, after 3 hours at −65°, only the adduct to the carbonyl group [2-(4-cyanophenyl)-2-hexanol] in 48% yield [Imamoto et al., *J. Org. Chem.*, 49, 3904 (1984)]. The reagent prepared from n-butylmagnesium chloride and anhydrous cerium chloride adds to phenylacetonitrile only once to give the imine in low yield [Imamoto et al. *J. Am. Chem. Soc.*, 111, 4392 (1989)]. Derivatives of secondary carbinamines have been prepared by addition of organocerium reagents to N-benzylaldimines [Reetz et al. *Angew. Chem. Int. Ed. Engl.*, 30, 103 (1991)], N,N-disubstituted hydrazones [Denmark et al., *J. Am. Chem. Soc.*, 109, 2224 (1987); *Synlett* 1989, 20], and oxime ethers [Fujioka et al., *Chem. Pharm. Bull.*, 37, 602 (1989); Ukaji et al., *Chemistry Lett.*, 1991, 173].

SUMMARY OF THE INVENTION

The novel process of this invention consists of allowing nitriles to react with organolanthanide reagents to give tertiary carbinamines I. The invention will be described in terms of a preferred embodiment; the use of organocerium reagents. The preferred process is summarized illustratively in the following reaction schemes and described specifically in Examples 1–4 and 7–20.

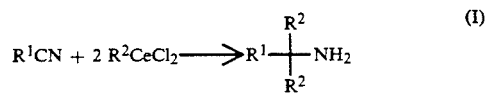

It further consists of allowing imines to react with organocerium reagents to give tertiary carbinamines II: this process permits the preparation of tertiary carbinamines with three different groups on the tertiary carbon, Examples 5 and 6. The groups $R^3$, $R^4$, and $R^5$ may independently be the same or different.

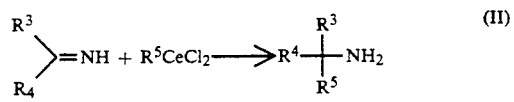

$R^1$, $R^3$, and $R^4$ may be any group that does not react with organocerium reagents, such as alkyl, alkenyl, cycloalkyl, cyclic ethers such as tetrahydrofuryl or tetrahydropyranyl, cyclic thioethers such as tetrahydrothienyl, cyclic tertiary amines such as N-alkylpiperidinyl, or aryl, or heteroaryl, all optionally substituted with groups that do not react with organocerium reagents, such as alkyl, alkenyl, alkyl- or arylethynyl, aryl, heteroaryl, halogens, alkoxy, alkylthio or tertiary amino. Substituents on $R^1$, $R^3$, and $R^4$ may also be groups that react with organocerium reagents, such as hydroxyl, primary and secondary amino, and sulfhydryl, which form salts, and require an excess of organocerium reagent. Substituents on $R^1$, $R^3$, and $R^4$ that react with organocerium reagents may be present, but they are converted into different groups: formyl groups are known to be converted into secondary carbinols, ketones and esters into tertiary carbinols. When two or three cyano or imine groups are present in the same molecule, all may be converted into tertiary carbinamines.

$R^2$ and $R^5$ are primary or secondary alkyl of up to about 20 carbon atoms, or aryl, furyl, benzofuryl, thienyl, or benzothienyl optionally substituted with alkyl, alkenyl, aryl, fluorine, chlorine, alkoxy, alkylthio, or tertiary amino.

DETAILED DESCRIPTION OF THE INVENTION

The organocerium reagents are prepared according to Imamoto et al. [*J. Org. Chem.* 49, 3904 (1984)] from one molar equivalents each of organolithium reagents $R^2Li$ or $R^5Li$ and anhydrous cerium chloride in tetrahydrofuran. A ratio of 2:1 or 3:1 may also be employed. Anhydrous lanthanum chloride, praseodymium chloride, neodymium chloride or ytterbium chloride may be substituted for cerium chloride, but the latter is preferred because of its low cost. An excess over the calculated amount of organocerium reagent is preferred in most cases since it increases the yields of tertiary carbinamines. The reactions are carried out at $-70°$ to $+60°$ in tetrahydrofuran in the absence of moisture under nitrogen or argon. Solvents in which the organolithium reagents are prepared, such as ether, pentane, or cyclohexane, do not interfere with the reaction. Products are isolated by addition of water or, preferably, aqueous ammonium hydroxide, and extraction into an organic solvent such as methylene chloride or toluene. Non-basic products may be removed by extraction of the tertiary carbinamines into dilute hydrochloric or phosphoric acid followed by liberation of the free bases with aqueous sodium or ammonium hydroxide.

The processes described herein provide a simple route to tertiary carbinamines. Compounds of this type are known, for instance, to be antiviral agents: Aldrich et. al., *J. Med. Chem.*, -535 (1974); E. I. du Pont de Nemours & Co., British Patent 1,069,563. The compound of Example 11 herein was reported to be comparable in antiviral activity to amantadine.

The term "alkyl" as used herein means a saturated hydrocarbon radical having from one to 20 carbon atoms, which can be a straight or branched chain. Representative of such radicals are methyl, ethyl, n-propyl, isopropyl, n-butyl, sec-butyl, isobutyl, octyl and the like.

The term "aryl" as used herein means aromatic groups of up to three rings, each ring which may be 5- or 6- membered, and which may include from zero to four heteroatoms. Representative aryls include phenyl, naphthyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, and the like.

The invention can be further understood by the following examples in which temperatures are in degrees Centigrade and parts and percentages are by weight unless otherwise indicated. For simplicity, organocerium reagents are written as $RCeCl_2$, even though the exact nature of these reagents is unknown.

EXAMPLES

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof on either scope or spirit. Those of skill in the art will readily understand that known variations of the conditions and processes of the preparative procedures described in these examples can be used to prepare the compounds of the present invention, and the pharmaceutical compositions comprising such compounds.

All starting materials employed in the examples are commercially available except as may be indicated. Most of the starting materials were obtained from Aldrich Chemical Co., Milwaukee, Wis.

All patents and publications referred to in the examples, and throughout the specifications, are hereby incorporated herein by reference, without admission that such is prior art.

EXAMPLE 1

α,α-Dibutylbenzylamine

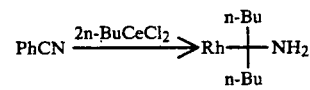

Cerium chloride heptahydrate (15.0 g 40.2 mmol) was dried with magnetic stirring at 140°–150° under 0.1 mm vacuum for two hours. Nitrogen was admitted and the flask containing the solid was cooled with an ice bath. Anhydrous tetrahydrofuran (80 mL) was added and the suspension was stirred at room temperature for 2 hours. n-Butyllithium (24 mL of a 1.6M solution in hexanes, 40 mmol) was added below $-55°$ by syringe, and the mixture was stirred in a dry ice acetone bath for 30 minutes. Benzonitrile (1.34 g, 13 mmol) in 2 mL of anhydrous tetrahydrofuran was added, and the cooling bath was removed. Aqueous ammonium hydroxide (25 mL) was added after 2 hours, keeping the temperature below 0°, and the mixture was filtered with the aid of celite TM. The solids were washed three times with methylene chloride, and the aqueous layer of the filtrate was extracted twice with methylene chloride. The combined organic phases were dried and concentrated and the residue was short-path distilled to give 2.53 g (90%) of the title compound distilling at a bath temperature of 80°–130° (0.003 mm). $^1$H-NMR (in $CDCl_3$) ∂0.8 (t, J=6 Hz, 6H), 1.0 (m, 2H), 1.2 (m, 6H), 1.4 (br, 2H), 1.6 (m, 2H), 1.8 (m, 2H), 7.2–7.4 (m, 5H).

Anal. Calcd. for $C_{15}H_{25}N$: C, 82.13; H, 11.49; N, 6.39. Found: C, 81.80; H, 11.52; N, 6.14.

The hydrochloride had mp 209°–216° after crystallization from water.

Anal. Calcd. for $C_{15}H_{26}ClN$: C, 70.42; H, 10.24; N, 5.48. Found: C, 70.27; H, 10.34; N, 5.45.

The yield of α,α-dibutylbenzylamine was identical when the reaction was carried out at $-65°$ for 3 hours. When the ratio of benzonitrile: cerium chloride: n-butyllithium was 1.3:2:4, the yield was 60% and when it was 1:1:3, the yield was 44%. The yields with other lanthanide trichlorides were: lanthanum chloride, 20%; praseodymium chloride, 74%; neodymium chloride, 86%; ytterbium chloride, 74%.

EXAMPLE 2

Triphenylmethylamine

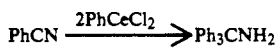

Cerium chloride heptahydrate (15.0 g, 40 mmol) was dried and stirred with 80 mL of dry tetrahydrofuran as described in Example 1. To this was added by cannulation below −50° a solution of phenyllithium prepared by addition of 16 mL of 2.5M n-butyllithium in hexanes (40 mmol) to 6.28 g (40 mmol) of bromobenzene in 15 mL of tetrahydrofuran below −40°. The mixture was stirred in a dry ice-acetone bath for 30 minutes, and 1.34 g (13 mmol) of benzonitrile in 2 mL of tetrahydrofuran were added. The bath was removed and the mixture was stirred for 2 hours. Isolation as described in Example 1 gave 3.30 g (98%) of triphenylmethylamine, identical by infrared, $^1$H and $^{13}$C NMR spectroscopy with an authentic sample.

EXAMPLE 3

α,α,α′,α′-Tetrabutyl-1,4-benzenedimethylamine

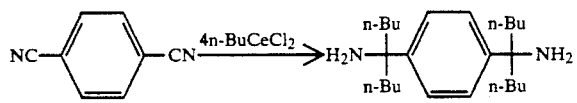

Following the procedure of Example 1, but adding, in place of benzonitrile, 0.85 g (6.6 mmol) of 1,4-dicyanobenzene as a solid, there was obtained 1.90 g (79%) of the title compound, distilling at a bath temperature of 175°–190° (0.001 mm). $^1$H NMR (in CDCl$_3$):

∂ 0.8 (t, J=7 Hz, 12H), 0.9–1.8 (m, 28H), 7.2 (s, 4H).

Anal. Calcd. for C$_{24}$H$_{44}$N$_2$: C, 79.93; H, 12.30; N, 7.77. Found: C, 79.91; H, 12.42; N, 7.68.

The dihydrochloride melted at 297°–302° after crystallization from ethanol.

Anal. Calcd. for C$_{22}$H$_{46}$Cl$_2$N$_2$: C, 66.49; H, 10.69; N, 6.46. Found: C, 66.04; H, 10.90; N, 6.29.

EXAMPLE 4 trans-2-Methyl-4-phenyl-3-buten-2-amine

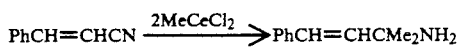

Following the procedure of Example 1, but using 29 mL of 1.4M methyllithium in ether (40 mmol) and 2.58 g (20 mmol) of trans-cinnamonitrile, there was obtained 2.48 g (77%) of the title compound, distilling at a bath temperature of 110°–140° (5 mm). $^1$H NMR (in CDCl$_3$):

∂ 1.3 (s, 6H), 1.4 (br, 2H); 6.3 (d, J=16 Hz, 1H); 6.4 (d, J=16 Hz, 1H); 7.2–7.4 (m, 5H). The hydrochloride had mp 218°–219° after crystallization from 2-propanol.

Anal. Calcd. for C$_{11}$H$_{16}$ClN: C, 66.83; H, 8.16; N, 7.08. Found: C, 66.77; H, 8.20; N, 7.03.

When 1.29 g (10 mmol) of trans-cinnamonitrile were used in the above experiment, 2,3-dimethyl-4-phenyl-2-butanamine was obtained in 46% yield.

EXAMPLE 5

2,2-Diphenylpentanamine

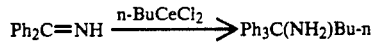

A suspension of 40 mmol of n-BuCeCl$_2$ was prepared as described in Example 1. A solution of 2.37 g (13.1 mmol) of benzophenone imine in 5 mL of tetrahydrofuran was added below −50°, the bath was removed, and the reaction was quenched after two hours and the product isolated as described in Example 1. The crude product was dissolved in ethanol and a solution of hydrogen chloride in ether was added to give a precipitate of 2.86 g (79%) of 2,2-diphenylpentanamine hydrochloride, mp 237°–239°.

Anal. Calcd. for C$_{17}$H$_{22}$ClN: C, 74.03; H, 8.04; N, 5.08. Found: C, 73.88; H, 8.10; N, 5.02.

$^{13}$C NMR of the free base (in CDCl$_3$): ∂13.983, 23.166, 26.288, 42.375, 60.905, 126.093, 126.514, 127.952, 148.945,

EXAMPLE 6

α-Methyl-α-butylbenzylamine

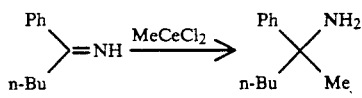

A suspension of MeCeCl$_2$ was prepared as described in Example 1 from 7.5 g (20 mmol) of cerium chloride heptahydrate, 40 mL of tetrahydrofuran, and 14 mL of 1.4M methyllithium in ether (20 mmol). To this was added below −60° a solution of 1.35 g (8.4 mmol) of valerophenone imine in 5 mL of tetrahydrofuran. The mixture was stirred in a dry ice-acetone bath for 3 hours, treated below −40° slowly with 12 mL of conc. ammonium hydroxide solution, and allowed to come to room temperature. Celite ™ was added, the mixture was filtered, and the solids were washed several times with methylene chloride. The dried organic layer of the filtrates was concentrated. The crude product (1.39 g) still contained ca. 10% unreacted imine as shown by $^1$H NMR spectroscopy. The product was dissolved in toluene and stirred with 3% phosphoric acid for 2 hours. The toluene layer was washed twice with water, and the combined aqueous phases were washed once with toluene and made basic with conc. ammonium hydroxide solution. Extraction with methylene chloride and short-path distillation of the crude product gave 0.83 g (56%) of the title compound., distilling at a bath temperature of 110° (0.005 mm). $^1$H NMR (in CDCl$_3$) ∂ 0.8 (t, J=7 Hz, 3H), 1.0–1.3 (m, 4H); 1.4 (s, 3H), 1.5 (br, 2H), 1.6–1.8 (m, 2H), 7.2–7.5 (m, 5H). The hydrochloride had mp 153°–156° after crystallization from acetonitrile.

Anal. Calcd. for C$_{12}$H$_{20}$ClN C, 67.43; H, 9.43; N, 6.55. Found: C, 67.40; H, 9.55. N, 6.49.

The starting material, valerophenone imine, was prepared as follows: to 16 mL of 2.5M n-butyllithium in hexanes (40 mmol) and 15 mL of tetrahydrofuran was added below −10° 3.10 g (30 mmol) of benzonitrile. The mixture was stirred in an ice bath for 30 minutes and treated with water, keeping the temperature below 10°. Extraction with ether and short-path distillation of the crude product gave 4.44 g (92%) of valerophenone imine, distilling at a bath temperature 120° (0.002 mm).

The reactions in Table 1 were carried out as described in Example 1. Where required, purification was effected as described in Example 6.

TABLE 1

$$R^1CN + 2\ R^2CeCl_2 \longrightarrow R^1\underset{R^2}{\overset{R^2}{|}}NH_2$$

| Ex. # | $R^1$ | $R^2$ | Yield (%) | Mp of HCl salt |
|---|---|---|---|---|
| 7 | n-$C_{11}H_{23}$ | Me | 38 | 118–119° |
| 8 | i-Pr | i-Pr | 32 | >320° |
| 9 | t-Bu | n-Bu | 82 | |
| 10 | cycloheptyl | Me | 42 | |
| 11 | 1-adamantyl | Me | 75 | >320° |
| 12 | 1-naphthyl | Me | 41 | |
| 13 | Ph | i-Pr | 50 | >320 |
| 14 | Ph | sec-Bu | 64 | >320° |
| 15 | 4-Ph$C_6H_4$ | i-Pr | 47 | 253–266° (dec.) |
| 16 | Me$C_6H_4CH_2$ | n-Bu | 16 | |
| 17 | 4-pyridyl | n-Bu | 92 | 218–222° (dec.) |
| 18 | 1-phenethyl-4-piperidyl | n-Bu | 90 | 270–272° (dec.) |
| 19 | 2-furyl | 2-furyl | 89 | |
| 20 | i-Pr | 2-thienyl | 14 | |

Footnotes to Table 1:

| | | Analyses of HCl Salts | | | | | |
|---|---|---|---|---|---|---|---|
| | | Calculated | | | Found | | |
| Ex. # | Formula | C | H | N | C | H | N |
| 7 | $C_{14}H_{32}ClN$ | 67.30 | 12.9 | 15.61 | 67.54 | 13.03 | 5.54 |
| 8 | $C_{10}H_{24}ClN$ | 61.99 | 12.49 | 7.23 | 62.19 | 12.75 | 7.08 |
| 11 | $C_{13}H_{24}ClN$ | 67.79 | 10.53 | 6.10 | 67.79 | 10.76 | 6.03 |
| 13 | $C_{13}H_{22}ClN$ | 68.55 | 9.75 | 6.15 | 68.55 | 9.77 | 6.03 |
| 14 | $C_{15}H_{26}ClN$ | 70.42 | 10.24 | 5.48 | 70.47 | 10.38 | 5.34 |
| 15 | $C_{19}H_{20}ClN$ | 75.10 | 8.62 | 4.61 | 74.98 | 8.74 | 4.44 |
| 17[a] | $C_{14}H_{26}Cl_2N_2$ | 57.38 | 8.94 | 9.55 | 57.27 | 9.02 | 9.55 |
| 18[a,b] | $C_{22}H_{42}Cl_2N_2O$ | 62.69 | 10.04 | 6.65 | 62.75 | 10.19 | 6.50 |

[a]Dihydrochloride.
[b]The salt crystallized with one mole of water

| | High-Resolution Mass Spectra of Free Bases $(M + H)^+$ | | |
|---|---|---|---|
| Ex. # | Formula | Calcd. | Found |
| 9 | $C_{13}H_{29}N$ | 200.2378 | 200.2383 |
| 10 | $C_{10}H_{21}N$ | 156.1752 | 156.1743 |
| 12 | $C_{13}H_{15}N$ | 186.1283 | 186.1292 |
| 16 | $C_{17}H_{29}N$ | 248.2378 | 248.2376 |
| 19 | $C_{13}H_{11}NO_3$ | 230.0817 | 230.0806 |
| 20 | $C_{12}H_{15}NS_2$ | 238.0736 | 238.0724 |

While the various aspects of the present invention are described herein with some particularity, those of skill in the art will recognize numerous modifications and variations which remain within the spirit of the invention. These modifications and variations are within the scope of the inventions as described and claimed herein.

What is claimed is:

1. A method of making a tertiary carbinamine of the formula

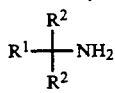

which comprises reacting a nitrile of the formula $R^1CN$ with an organolanthanide reagent which is obtained by reacting a compound of the formula $R^2Li$ with a reagent selected from the group consisting essentially of anhydrous lanthanum chloride, praseodymium chloride, neodymium chloride, ytterbium chloride and cerium chloride wherein $R^1$ is selected from the group consisting essentially of alkyl, alkenyl, cycloalkyl, cyclic ethers, cyclic thioethers, cyclic tertiary amines, or aryl, or heteroaryl; $R^1$ being optionally substituted with a group that does not react with organolanthanide reagents; said group being selected from the group consisting essentially or alkyl, alkenyl, alkyl- or arylethynyl, aryl, heteroaryl, halo, alkoxy, alkylthio or tertiary amino, or $R^1$ may be optionally substituted with a group which does react with organolanthide reagents, and which group is selected from the group consisting essentially of hydroxyl, primary and secondary amino, sulfhydryl, formyl, ketones, esters, cyano, or imino; and $R^2$ is a primary or secondary alkyl of up to about 20 carbon atoms, or aryl, furyl, benzofuryl, thienyl, or benzothienyl optionally substituted with alkyl, alkenyl, aryl, fluorine, chlorine, alkoxy, alkylthio, or tertiary amino.

2. The method of claim 1 wherein the organolanthanide reagent is derived from cerium chloride.

3. The method of claim 1 wherein $R^1$ is substituted with a group which does not react with an organolanthanide reagents said group being selected from the group consisting essentially of alkyl, alkenyl, alkyl or arylethynyl, heteroaryl, halo, alkoxy, alkylthio, or tertiary amino.

4. The method of claim 1 wherein the organolanthanide reagent is present in the excess over the calculated amount necessary for the reaction.

5. A method of making a tertiary carbinamine of the formula:

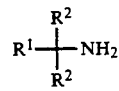

which comprises reacting a nitrile of the formula $R^1CN$ with an organocerium reagent of the formula $R^2CeCl_2$, wherein $R^1$, is selected from the group consisting essentially of alkyl, alkenyl, cycloalkyl, cyclic ethers, cyclic thioethers, cyclic tertiary amines, or aryl, or heteroaryl; $R^1$, being optionally substituted with a group that does not react with organocerium reagents; said group being selected from the group consisting essentially of alkyl, alkenyl, alkyl- or arylethynyl, aryl, heteroaryl, halo, alkoxy, alkylthio or tertiary amino, or $R^1$ may be optionally substituted with a group which does react with organocerium reagents, and which group is selected from the group consisting essentially of hydroxyl, primary and secondary amino, sulfhydryl, formyl, ketones, esters, cyano, or imino; and $R^2$ is a primary or secondary alkyl of up to about 20 carbon atoms, or aryl, furyl, benzofuryl, thienyl, or benzothienyl optionally substituted with alkyl, alkenyl, aryl, fluorine, chlorine, alkoxy, alkylthio, or tertiary amino.

6. The method of claim 1 wherein $R^2$ is selected from the group consisting essentially of primary or secondary alkyl, aryl, furyl, benzofuryl, thienyl, or benzothienyl optionally substituted with alkyl, alkenyl, aryl, fluoro, chloro, alkoxy, alkylthio or tertiary amino.

7. The method of claim 6 wherein $R^1$ is a group which does not react with an organocerium reagent, which group is selected from the group consisting essentially of alkyl, alkenyl, cycloalkyl, cyclic ethers, cyclic thioethers, cyclic tertiary amines, or aryl or heteroaryl, all optionally substituted with a group that does not react with organocerium reagents, said group being selected from the group consisting essentially of alkly, alkenyl, alkyl or arylethynyl, aryl, heteroaryl, halo, alkoxy, alkylthio, or tertiary amino.

8. The method of claim 6 wherein the organocerium reagent is present in an excess over the calculated amount necessary for the reaction.

9. The method of claim 8 wherein the reactions are conducted at a temperature of from about −70° C. to about +60° C.

10. The method of claim 9 wherein the reactions are carried out in tetrahydrofuran under a nitrogen or argon atmosphere.

11. The method of claim 10 including the step of isolation of the product by the addition of aqueous ammonia hydroxide to the crude product and extraction of the product with an organic solvent.

12. The method of claim 11 wherein the organic solvent is methylene chloride or toluene.

13. The method of claim 5 wherein R1 is substituted with a group which does not react with an organocerium reagent said group being selected from the group consisting essentially of alkyl, alkenyl, alkyl or arylethynyl, aryl, heteroaryl, halo, alkoxy, alkylthio, or tertiary amino.

14. The method of claim 7 wherein the cyclic ethers are tetrahydrofuryl or tetrahydropyranyl and the cyclic thioether is tetrahydrothienyl and the cyclic tertiary amine is N-alkylpiperidinyl.

* * * * *